United States Patent [19]

Watanabe et al.

[11] Patent Number: 5,354,864
[45] Date of Patent: Oct. 11, 1994

[54] 3-(9-ACRIDINYLAMINO)-5-HYDROXYME-THYLANILINE DERIVATIVES AS ANTICANCER AGENTS

[75] Inventors: Kyoichi A. Watanabe, Rye Brook; Grazyna Ciszewska, Jamaica; Tsann-Long Su, Baldwin Place; Ting-Chao Chou, New York, all of N.Y.

[73] Assignee: Sloan-Kettering Institute for Cancer Research, New York, N.Y.

[21] Appl. No.: 886,980

[22] Filed: May 21, 1992

[51] Int. Cl.$^5$ .............................................. A61K 31/47
[52] U.S. Cl. ................................................... 546/106
[58] Field of Search ...................... 514/297; 546/106; A61K 31/47

[56]  References Cited

U.S. PATENT DOCUMENTS

| | | | |
|---|---|---|---|
| 2,419,200 | 4/1947 | Burckhalter | 546/106 |
| 4,603,125 | 7/1986 | Atwell et al. | 514/297 |
| 4,704,397 | 11/1987 | Fisher et al. | 514/297 |
| 4,815,447 | 3/1989 | Mills | 600/1 |
| 4,815,448 | 3/1989 | Mills | 600/2 |
| 5,229,395 | 7/1993 | Watanabe et al. | 514/297 |

FOREIGN PATENT DOCUMENTS 17-12796  7/1942  Japan .................................. 514/297

OTHER PUBLICATIONS

Watanabe et al, NIH Grant Request, Award CA-18856 approved, 1990.
Mills et al Chem. Abstr vol. 116 entry 37120d (1991).
Cain et al. Jour. Med. Chem. vol. 19, pp. 1124-1129 (1976).

(List continued on next page.)

*Primary Examiner*—Donald G. Daus
*Attorney, Agent, or Firm*—John P. White

[57]  ABSTRACT

The present invention provides a compound having the structure:

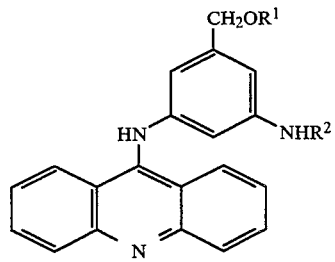

wherein $R^1$ and $R^2$ are independently the same or different and are hydrogen, an acetyl group; an acyl group having the formula $—CO(CH_2)_nCOCH_3$, wherein n=1-3; $—CO(CH_2)_nCOOM$, wherein n=1-4 and M is hydrogen, Na or K; or $—(CH_2)_nCOOR$, wherein n=1-4 and R is hydrogen, Na, K or an alkyl group having 1 to 5 carbon atoms; a hydroxyalkyl group having the formula $—(CH_2)_nCH_2OH$, wherein n=1-4; a halo alkyl group having the formula $—(CH_2)_nCH_2X$, wherein n=1-4 and X is a chloro, bromo, or iodo group; a metal sulfonate ($—SO_3M$) wherein M is Na or K; a metal sulfinate ($—SO_2M$) wherein M is Na or K; a alkyl sulfonate ($—SO_3R$) wherein R is an alkyl group having 1 to 4 carbon atoms such as methyl, ethyl, n-propyl or i-propyl; an alkylsulfonyl group ($—SO_2R$) wherein R is an alkyl group having 1 to 4 carbon atoms such as methyl, ethyl, n-propyl or i-propyl; a metal alkylsulfonate having the formula $—(CH_2)_nSO_3M$ wherein n=2-3 and M is Na or K; a metal alkylsulfate having the formula $—(CH_2)_nOSO_3M$ wherein n=2-3, and M is Na or K; or a $\beta$-alanyl group.

The present invention also provides a process for synthesizing the above-identified compound, intermediate compounds produced thereby, a pharmaceutical composition comprising the above compounds as well as a method for inhibiting growth of tumor cells using these compounds.

3 Claims, No Drawings

OTHER PUBLICATIONS

Ferguson et al, Jour. Med. Chem. vol. 22 pp. 251–255 (1979).

Cain et al., Potential Antitumor Agents. 11. 9-Anilinoacridines, *J. Med. Chem* (1971), vol. 14, pp. 311–315.

Cain et al., Potential Antitumor Agents. 16.4'-(Acridin-9-ylamino) methanesulfonanilides, *J. Med. Chem.* (1975), vol. 18, pp. 1110–1117.

Corbett et al., Evaluation of Single Agents and Combinations of Chemotherapeutic Agents in Mouse Colon Carcinomas, *Cancer*, (1977), vol. 40, pp. 2660–2680.

Goldin et al., Current Results of the Screening Program at the Division of Cancer Treatment, National Cancer Institute, *Eur. J. Cancer*, (1981) vol. 17, pp. 129–142.

Legha et al., 4'(9'-Acridinylamino) methanesulfon-m-anisidide (AMSA): A New Drug Effective in the Treatment of Adult Acute Leukemia, *Ann. Internal. Med.*, (1980), vol. 93 (Part I), pp. 17–21.

Cabanillas et al., Initial Experience with AMSA as Single Agent Treatment Against Malignant Lymphoproliferative Disorders, *Blood*, (1981) vol. 57, pp. 614–616.

Arlin et al., Phase I and II Trial of 4'(9-Acridinylamino) methanesulfon-m anisidide in Patients with Acute Leukemia, *Cancer Res.*, (1980), vol. 40 pp. 3304–3306.

Laster et al., Therapeutic Synergism (TS) of N-(4-9-Acridinylamino)-3-methoxyphenyl) methanesulfonamide (m-AMSA) or 1, 4-Dihydroxy-5, 8-bis [[2-Hydroxyethyl]Amino]-9, 10-Anthracenedione (DiOHA) Plus cis-Diamminedichloroplatinum (cis-DDPt) Against P338/O Leukemia, *Proc. Am. Ass. Res.*, (1980), vol. 21, p. 271, abstract 1086.

Caspar et al., Phase II Evaluation of 4'(9-Acridinylamino)-methansulfonanisidide (AMSA) in Patients with Non-Small Lung Cancer, *Cancer Treat. Rep.*, (1980), vol. 64, pp. 345–347.

Nelson et al., Mechanism of Antitumor Drug Action: Poisoning of Mammalian DNA Topoisomerase II on DNA by 4'(9-Acridinylamino)-methanesulfon-m-anisidide, *Proc. Natl. Acad. Sci* USA, (Mar., 1984), vol. 81, pp. 1361–1365.

Pommier et al., Correlations between Intercalator-induced DNA Strand Breaks and Sister Chromatid Exchanges, Mutations, and Cytoxicity in Chinese Hamster Cells, *Cancer Res.*, (1985), vol. 45, pp. 3143–3149.

Wilson et al., Comparison of the Mutagenic and Clastogenic Activity of Amsacrine and other DNA-Intercalating Drugs in Cultured V79 Chinese Hamster Cells, *Cancer Res.*, (1984), vol. 44, pp. 4420–4431.

Khan et al., Mechanism of the Hydrolysis of m-AMSA (NSC 249992), *Proc. Am. Ass. Cancer Res.*, (1980), vol. 21, p. 306, Abstract No. 1227.

Shoemaker et al., Identification of the Principal Biliary Metabolite of 4'-(9-Acridinylamino)-methanesulfon-m-anisidide in rats, *Drug Metab. Disp.*, (1982), vol. 10, pp. 35–39.

3-(9-ACRIDINYLAMINO)-5-HYDROXYMETHYLANILINE DERIVATIVES AS ANTICANCER AGENTS

This application described herein was made in the course of work under grants from the National Cancer Institute, National Institutes of Health, U.S. Department of Health and Human Services (Grants CA-08748 and CA-18856). The U.S. Government has certain rights in this invention.

BACKGROUND OF THE INVENTION

Throughout this application various publications are referenced. The disclosures of these publications in their entireties are hereby incorporated by reference into this application in order to more fully describe the state of the art to which this invention pertains.

It has long been known that acridine derivatives, particularly 9-aminoacridines, bind preferentially to nucleic acids in living cells. Many anilinoacridine derivatives, for example, have been synthesized and were demonstrated to have outstanding experimental antitumor activity and a broad spectrum of biological activities Cain et al., *J. Med. Chem.* 1971; 14:311. Among these compounds, amsacrine [4'-(9-acridinylamino)methanesulfon-m-anisidide, m-AMSA] was reported to have high activity against the L1210 leukemia Cain et al., *J. Med. Chem.* 1975; 18:1110 and against a spectrum of experimental tumors Corbett et al., *Cancer*, 1977; 40:2660; Goldin et al., *Eur. J. Cancer*, 1981; 17:129. The clinically useful m-AMSA is an extremely promising drug in the treatment of leukemia Legha et al., *Ann. Internal. Med.*, 1980; 93 (part 1):17 and malignant lymphoma Cabanillas et al., *Blood*, 1981; 57:614, particularly in combination with other cytotoxic agents Arlin et al., *Cancer Res.*, 1980; 40:3304; Laster et al., *Proc. Am. Ass. Cancer Res.*, 1980; 21:271. The drug, though, was inactive against a number of solid tumors during Phase II trials Casper et al., *Cancer Treat. Rep.*, 1980; 64:345. m-AMSA is a DNA intercalator and topoisomerase II inhibitor Nelson et al., *Proceedings of the National Academy of Science*, 1984; 81:1361; Pommier et al., *Cancer Res.*, 1985; 45:3143. The cytotoxicity of m-AMSA later revealed that this agent induced chromosomal aberrations and DNA damage Wilson et al., *Cancer Res.*, 1984; 44:4420.

9-Anilinoacridines undergo nucleophilic attack by thiols to produce inactive products forming protein adducts linked by a thiol group to the C-9 position of the acridine and released side-chain Khan et al., *Proc. Am. Ass. Cancer Res.*, 1980; 21:306. The half life of m-AMSA in the presence of fresh mouse blood at 37° C. is about 23 minutes. More recently, an alternative mechanism was suggested for degradation of m-AMSA by mammalian liver extracts, in which the anilino ring is oxidized to a quinoneimine, then conjugated with glutathione to form the inactive 5'-thio metabolite Shoemake et al., *Drug Metab. Disp.*, 1982; 10:35. The inventors have synthesized 3-(9-acridinylamino)-5-hydroxymethylaniline derivatives, in which, with both amino and hydroxymethyl functions in meta-position to 9-acridinylamino, it would not be possible to form a quinoneimine open for the nucleophilic attack of glutathione. These compounds would thus be tolerant under biological degradation. The inventors discovered that the derivatives of 3-(9-acridinylamino)-5-hydroxymethylanine are inhibitors of DNA topoisomerase II and show inhibition of tumor growth in vitro and in vivo (Tables 1 and 2). On the basis of the above considerations and discoveries, the present invention is submitted.

SUMMARY OF THE INVENTION

The present invention provides a compound having the structure:

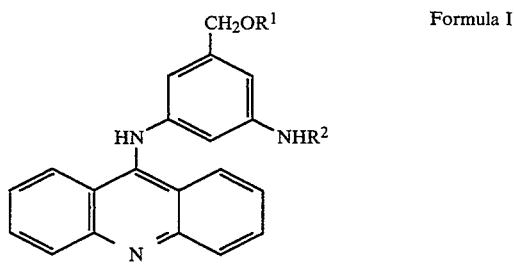

Formula I wherein $R^1$ and $R^2$ are independently the same or different and are hydrogen, an acetyl group;
an acyl group having the formula:
—$CO(CH_2)_nCOCH_3$, wherein n=1–3;
—$CO(CH_2)_nCOOM$, wherein n=1–4 and M is hydrogen, Na or K; or
—$(CH_2)_nCOOR$, wherein n=1–4 and R is hydrogen, Na, K or an alkyl group having 1 to 5 carbon atoms;
a hydroxyalkyl group having the formula —$(CH_2)_nCH_2OH$, wherein n=1–4; a halo alkyl group having the formula —$(CH_2)_nCH_2X$, wherein n=1–4 and X is a chloro, bromo, or iodo group; a metal sulfonate (—$SO_3M$) wherein M is Na or K; a metal sulfinate (—$SO_2M$) wherein M is Na or K; a alkyl sulfonate (—$SO_3R$) wherein R is an alkyl group having 1 to 4 carbon atoms such as methyl, ethyl, n-propyl or i-propyl; an alkylsulfonyl group (—$SO_2R$) wherein R is an alkyl group having 1 to 4 carbon atoms such as methyl, ethyl, n-propyl or i-propyl;
a metal alkylsulfonate having the formula:
—$(CH_2)_nSO_3M$ wherein n=2–3 and M is Na or K;
a metal alkylsulfate having the formula:
—$(CH_2)_nOSO_3M$ wherein n=2–3, and M is Na or K;
or a β-alanyl group.

The present invention also provides a process for synthesizing the compounds above which comprises:

(a) contacting 9-chloroacridine with 3,5-diaminobenzyl alcohol under suitable conditions to form 3-(9-acridinylamino)-5-hydroxymethylaniline:

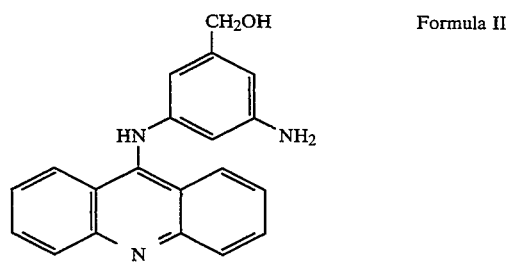

Formula II (b) treating the compound formed in step (a) under suitable conditions to form a compound having the structure:

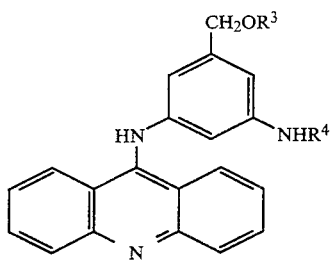

Formula III wherein each of $R^3$ and $R^4$ are independently the same or different and are hydrogen or an alkylester group having the formula $-(CH_2)_nCOOR$, wherein $n=1-4$ and R is an alkyl group having 1 to 4 carbon atoms.

(c) treating the compound formed in step (b) under suitable conditions to form a compound having the structure:

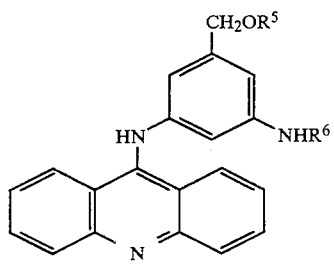

Formula IV wherein each of $R^5$ and $R^6$ are independently the same or different and are hydrogen or a hydroxyalkyl group having the formula $-(CH_2)_nCH_2OH$, wherein $n=1-4$.

(d) treating the compound formed in step (c) under suitable conditions to form a compound having the structure:

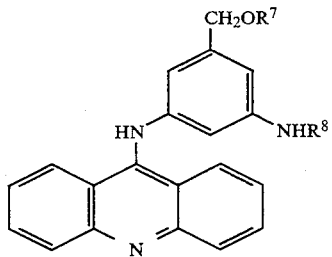

Formula V wherein $R^7$ and $R^8$ are independently the same or different and are a halo alkyl group having the formula $-(CH_2)_nCH_2X$, wherein $n=1-4$ and X is a chloro, bromo or iodo group.

(e) treating the compound formed in steps (a), (b), (c), or (d) under suitable conditions to form a compound having the structure:

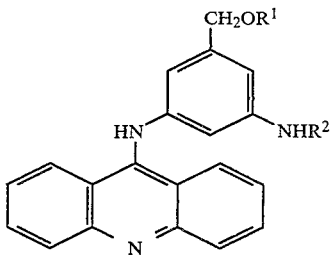

Formula I wherein $R^1$ and $R^2$ are independently the same or different as defined previously.

The present invention also provides a pharmaceutical composition which comprises an amount of a compound of Formula I and a pharmaceutically acceptable carrier.

The present invention further provides a method of inhibiting growth of tumor cells which comprises contacting the tumor cells with an effective amount of one of the compounds of Formula I, to inhibit growth of tumor cells.

DETAILED DESCRIPTION OF THE INVENTION

The subject invention provides a compound having the structure:

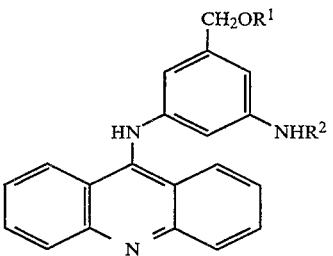

Formula I wherein $R^1$ and $R^2$ are independently the same or different and are hydrogen, an acetyl group;
an acyl group having the formula:
  $-CO(CH_2)_nCOCH_3$, wherein $n=1-3$;
  $-CO(CH_2)_nCOOM$, wherein $n=1-4$ and M is hydrogen, Na or K; or
  $-(CH_2)_nCOOR$, wherein $n=1-4$ and R is hydrogen, Na, K or an alkyl group having 1 to 5 carbon atoms;
a hydroxyalkyl group having the formula $-(CH_2)_nCH_2OH$, wherein $n=1-4$; a halo alkyl group having the formula $-(CH_2)_nCH_2X$, wherein $n=1-4$ and X is a chloro, bromo, or iodo group; a metal sulfonate ($-SO_3M$) wherein M is Na or K; a metal sulfinate ($-SO_2M$) wherein M is Na or K; a alkyl sulfonate ($-SO_3R$) wherein R is an alkyl group having 1 to 4 carbon atoms such as methyl, ethyl, n-propyl or i-propyl; an alkylsulfonyl group ($-SO_2R$) wherein R is an alkyl group having 1 to 4 carbon atoms such as methyl, ethyl, n-propyl or i-propyl;
a metal alkylsulfonate having the formula:
  $-(CH_2)_nSO_3M$ wherein $n=2-3$ and M is Na or K;
a metal alkylsulfate having the formula:
  $-(CH_2)_nOSO_3M$ wherein $n=2-3$, and M is Na or K;
or a β-alanyl group.

In the preferred embodiment, $R^1$ and $R^2$ are the same or different and are hydrogen, an acetyl group (—COCH₃), an acetoacetyl group (—COCH₂COCH₃), an acetonylacetyl group (—COCH₂CH₂COCH₃), an acetonylpropionyl group (—COCH₂CH₂CH₂COCH₃) group, an acetonylbutanoyl group (—COCH₂CH₂CH₂CH₂COCH₃), a methyl sulfonyl group (—SO₂Me), an ethyl sulfonyl group (—SO₃Et), a sodium, potassium, or ammonium sulfinate group (—SO₂Na), a sodium, potassium, or ammonium sulfonate group (—SO₃Na), a methane sulfonylethyl group (—CH₂CH₂SO₂Me), an ethane sufonylethyl group (—CH₂CH₂SO₂Et), a sodium (or potassium, or ammonium) ethylsulfinate group (—CH₂CH₂SO₂Na), a methane sulfonylpropyl group (—CH₂CH₂CH₂SO₂Me), an ethane sulfonylpropyl group (—CH₂CH₂CH₂SO₂Et), a sodium (or potassium, or ammonium) propyl sulfinate group (—CH₂CH₂CH₂SO₂Na), a methane ethylsulfonate group (—CH₂CH₂SO₃Me), an ethane sufonylethyl group (—CH₂CH₂SO₃Et), a sodium (or potassium, or ammonium ethylsulfinate group (—CH₂CH₂SO₃Na), a methane sulfonylpropyl group (—CH₂CH₂CH₂SO₃Me), an ethane sulfonylpropyl group (—CH₂CH₂CH₂SO₃Et), a sodium (or potassium, or ammonium) propyl sulfonate group (—CH₂CH₂CH₂SO₃Na), and a β-alanyl group.

In the most preferred embodiments, $R^1$ is H and $R^2$ is H; $R^1$ is CO(CH₂)₂COMe and $R^2$ is CO(CH₂)₂COMe; $R^1$ is H and $R^2$ is CO(CH₂)₂COMe; $R^1$ is CO(CH₂)₂COOH and $R^2$ is CO(CH₂)₂COOH; or $R^1$ is H and $R^2$ is CO(CH₂)₂COOH.

Compounds having the above-identified structure may be selected from, but are not limited to, the group consisting of:

3-(9-acridinylamino)-5-hydroxymethylaniline,
3-(9-acridinylamino)-5-hydroxymethyl-N-acetylaniline,
3-(9-acridinylamino)-N,O-bis(acetyl)-5-hydroxymethylaniline,
3-(9-acridinylamino)-5-acetoacetoxymethyl-N-acetylaniline,
3-(9-acridinylamino)-5-hydroxymethyl-N-acetoacetylaniline,
3-(9-acridinylamino)-N,O-bis(acetoacetyl)-5-hydroxymethylaniline,
3-(9-acridinylamino)-5-acetonylacetoxymethylaniline,
3-(9-acridinylamino)-5-hydroxymethyl-N-acetonylacetylaniline,
3-(9-acridinylamino)-N,O-bis(acetonylacetyl)-5-hydroxymethylaniline,
3-(9-acridinylamino)-5-acetonylpropionyloxymethylaniline,
3-(9-acridinylamino)-5-hydroxymethyl-N-acetonylpropionylaniline,
3-(9-acridinylamino)-N,O-bis(acetonylpropionyl)-5-hydroxymethylaniline,
3-(9-acridinylamino)-5-acetonylbutanoyloxymethylaniline,
3-(9-acridinylamino)-5-hydroxymethyl-N-acetonylbutanoylaniline,
3-(9-acridinylamino)-5-acetonylbutanoyloxymethyl-N-acetonylbutanoylaniline,
3-(9-acridinylamino)-5-malonyloxymethylaniline,
3-(9-acridinylamino)-5-hydroxymethyl-N-malonylaniline,
3-(9-acridinylamino)-5-malonyloxymethyl-N-malonylaniline,
3-(9-acridinylamino)-5-succinyloxymethyianiline,
3-(9-acridinylamino)-5-hydroxymethyl-N-succinylaniline,
3-(9-acridinylamino)-5-succinyloxymethyl-N-succinylaniline,
3-(9-acridinylamino)-5-glutaryloxymethylaniline,
3-(9-acridinylamino)-5-hydroxymethyl-N-glutarylaniline,
3-(9-acridinylamino)-5-glutaryloxymethyl-N-glutarylaniline,
3-(9-acridinylamino)-5-aminobenzyloxyacetic acid,
3-(9-acridinylamino)-5-hydroxymethylanilinoacetic acid,
sodium 3-(9-acridinylamino)-5-hydroxymethylanilinoacetate,
3-(9-acridinylamino)-N,O-bis(hydroxycarbonylmethyl)-5-hydroxymethylaniline,
3-[3-(9-acridinylamino)-5-aminobenzyloxy]propionic acid,
sodium 2-[3-(9-acridinylamino)-5-acetamidobenzyloxy]propionate,
3-[3-(9-acridinylamino)-5-hydroxymethylanilino]propionic acid,
sodium 2-[3-(9-acridinylamino)-5-hydroxymethylanilino]propionate,
3-[3-(9-acridinylamino)-5-hydroxycarbonylethoxymethylanilino]propionic acid,
sodium 2-[3-(9-acridinylamino)-5-hydroxycarbonylethoxymethylanilino]propionate
4-[3-(9-acridinylamino)-5-acetamidobenzyloxy]butanoic acid,
sodium 3-(9-acridinylamino)-5-aminobenzyloxybutyrate,
4-[3-(9-acridinylamino)-5-hydroxymethylanilino]butanoic acid,
sodium 4-[3-(9-acridinylamino)-5-hydroxymethylanilino]butyrate,
4-[3-(9-acridinylamino)-5-hydroxycarbonylpropyloxymethylanilino]butanoic acid,
sodium 4-[3-(9-acridinylamino)-5-hydroxycarbonylpropyloxymethylanilino]butyrate,
N-[3-(9-acridinylamino)-5-hydroxymethylphenyl]methanesulfonamide,
methyl 2-[3-(9-acridinylamino)-5-acetamidobenzyloxy]ethylsulfone,
methyl 2-[3-(9-acridinylamino)-5-aminobenzyloxy]ethylsulfone,
methyl 2-[3-(9-acridinylamino)-5-hydroxymethylanilino]ethyl sulfone,
3-(9-acridinylamino)-N,O-bis(methylsulfonylethyl)-5-hydroxymethylaniline,
methyl 3-[3-(9-acridinylamino)-5-aminobenzyloxy]propylsulfone,
methyl 3-[3-(9-acridinylamino)-5-hydroxymethylanilino]propyl sulfone,
methyl 3-(9-acridinylamino)-N,O-bis(methylsulfonylpropyl)-5-hydroxymethylaniline,
3-[3-(9-acridinylamino)-5-aminobenzyloxy]propyl sulfinic acid,
3-[3-(9-acridinylamino)-5-hydroxymethylanilino]propyl sulfinic acid,
3-(9-acridinylamino)-N,O-bis(sulfinylpropyl)-5-hydroxymethylaniline,
sodium 3-[3-(9-acridinylamino)-5-aminobenzyloxy]propyl sulfinate,
sodium 3-[3-(9-acridinylamino)-5-hydroxymethylanilino]propyl sulfinate,
3-(9-acridinylamino)-5-hydroxymethylaniline-N,O-bis(sodiumpropyl sulfinate),
methyl 2-[3-(9-acridinylamino)-5-aminobenzyloxy]ethyl sulfonate, methyl 2-[3-(9-acridinylamino)-5-acetamidobenzyloxy]ethyl sulfonate,
methyl 2-[3-(9-acridinylamino)-5-hydroxymethylanilino]ethyl sulfonate,
methyl 3-(9-acridinylamino)-5-hydroxymethylaniline-N,O-bis(ethyl sulfonate),
methyl 3-[3-(9-acridinylamino)-5-aminobenzyloxy]propyl sulfonate,
methyl 3-(9-acridinylamino)-5-acetamidobenzyloxy]propyl sulfonate,
methyl 3-[3-(9-acridinylamino)-5-hydroxymethylanilino]propyl sulfonate,
methyl 3-[3-(9-acridinylamino)-5-hydroxymethylaniline-N,O-bis(propyl sulfonate),
sodium 2-[3-(9-acridinylamino)-5-aminobenzyloxy]ethyl sulfonate,
sodium 2-[3-(9-acridinylamino)-5-acetamidobenzyloxy]ethyl sulfonate,
sodium 2-[3-(9-acridinylamino )-5-hydroxymethylanilino]ethyl sulfonate,
sodium 3-(9-acridinylamino)-5-hydroxymethylaniline-N,O-bis-(ethyl sulfonate),
sodium 3-[3-(9-acridinylamino)-5-aminobenzyloxy]propyl sulfonate,
sodium 3-[3-(9-acridinylamino)-5-acetamidobenzyloxy]propyl sulfonate,
sodium 3-[3-(9-acridinylamino)-5-hydroxymethylanilino]propyl sulfonate,
sodium 3-(9-acridinylamino)-5-hydroxymethylaniline-N,O-bis-(propyl sulfonate), or
3-(9-acridinylamino)-5-(β-alanyloxyethoxymethyl)aniline.

The present invention also provides a process for synthesizing the compounds above, which comprises:

(a) condensing 9-chloroacridine with 3,5-diaminobenzyl alcohol under suitable conditions to form 3-(9-acridinylamino)-5-hydroxymethylaniline (Formula II);

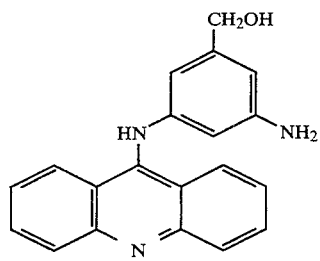

Formula II (b) treating the compound formed in step (a) under suitable conditions to form a compound having the structure

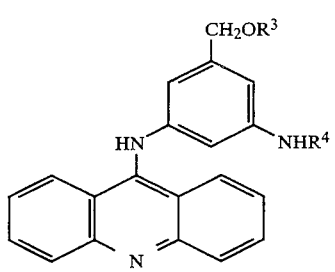

Formula III wherein $R^3$ and $R^4$ are independently the same or different and are hydrogen or an alkylester group having the formula $—(CH_2)_nCOOR$, wherein $n=1-4$ and R is an alkyl group having 1 to 4 carbon atoms;

(c) treating the compound formed in step (b) under suitable conditions to form a compound having the structure

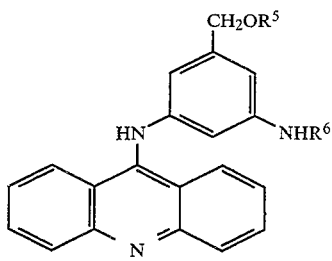

Formula IV wherein $R^5$ and $R^6$ are independently the same or different and are hydrogen or a hydroxyalkyl group having the formula $—(CH_2)_nCH_2OH$, wherein $n=1-4$;

(d) treating the compound formed in step (c) under suitable conditions to form a compound having the structure

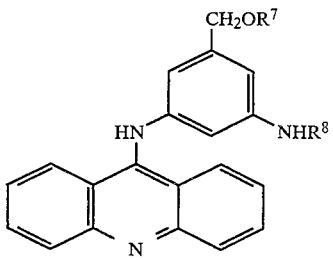

Formula V wherein $R^7$ and $R^8$ are independently the same or different and are a halo alkyl group having the formula $—(CH_2)_nCH_2X$, wherein $n=1-4$ and X is a chloro, bromo or iodo group;

(e) treating the compounds formed in steps (a), (b), (c), and (d) under suitable conditions to form a compound having the structure

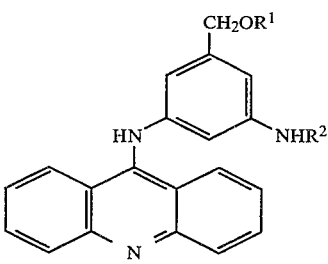

Formula I wherein $R^1$ and $R^2$ are independently the same or different as defined previously.

The contacting in step (a) comprises the condensation of 9-chloroacridine and 3,5-diaminobenzyl alcohol to form 3-(9-acridinylamino)-5-hydroxymethylaniline.

In the preferred embodiment, the contacting in step (a) is performed in the presence of an acid catalyst such as methylsulfonic acid, toluenesulfonic acid, benzenesulfonic acid, camphorsulfonic acid, and boron trihalide and other Lewis acids in an inert solvent such as chlorohydrocarbons methylene chloride, chloroform, ethylene dichloride, ethylene tetrachloride, or ethers such as tetrahydrofuran, dioxane or diethylether and the like, or in the presence of base such as sodium hydride, potassium hydride, triethylamine, N,N-dimethylaniline, N,N- diethylaniline, 4-(N,N-dimethylaminopyridine, 1,5-diazabicyclo[4.3.0]non-5-ene (DBN),1,8-diazabicyclo[5.5.0]-undec-7-ene (DBU), 2,6-di-tert-butylpyridine, 2,6-di-tert-butyl-4-methylpyridine and other organic bases, in a solvent such as chlorohydrocarbons methylene chloride, chloroform, ethylene dichloride, ethylene tetrachloride, or ethers such as tetrahydrofuran, dioxane or diethylether, or alcohols such as methanol, ethanol, propanol, or dimethylformamide and the like. Preferably, the contacting is carried out in a mixture of sodium hydride in dimethylformamide or triethylamine in methanol and the like, at room temperature for a period of 0.5 hour to 2 days.

The molar ratio of the reactants in step (a) of 9-acridine to 3,5-diaminobenzyl alcohol dihydrochloride to sodium hydride can be 2 to 1 to 5, but is preferably 1.2 to 1 to 3.

Upon completion of the reaction in step (a), ice-water is added to the reaction mixture and the precipitated product, 3-(9-acridinylamino)-5-hydroxyaniline, is collected by filtration. The product is treated with boiling chloroform to remove side product, 9-acridone, followed by purification by either recrystallization or chromatography.

The treating in step (b) comprises the alkylation of the compound of formula II with an ω-halo alkyl carboxylic acid ester to give the N- and/or O-alkylated compounds of formula III.

In one embodiment, the treating in step (b) comprises contacting the compound formed in step (a) with methyl or ethyl acrylate in water or alcohol such as methanol, ethanol, propanol and the like at a temperature range of 50° C. to 150° C. for a period of 30 minutes to 1 day to form the N-alkylated compounds of formula III, wherein $R^1$ is hydrogen and $R^2$ is an alkoxycarbonylethyl group having the formula —$CH_2CH_2COOR$, wherein R is a methyl or ethyl group.

In another embodiment, the treating in step (b) comprises contacting the compound formed in step (a) with an ω-halo alkyl carboxylic acid ester such as ethyl bromoacetate, ethyl 3-bromopropionate, ethyl 4-bromovalerate and the like to form N-alkylated compounds of formula III, wherein $R^1$ is hydrogen and $R^2$ is an alkoxycarbonylalkyl group having the formula —$(CH_2)_nCOOR$, wherein n=1–4 and R is methyl or ethyl group. In the preferred embodiment, the contacting is performed in the presence of base such as sodium hydroxide, potassium hydroxide, sodium carbonate, potassium carbonate, potassium tert-butoxide in a solvent at a temperature range of from 30° C. to 150° C. for a period of 0.5 hour to 2 days. The solvent is an alcohol such as methanol, ethanol, n-butanol and the like, or dimethylformamide.

The treating in step (c) comprises the reduction of the ester group(s) of the compounds formed in step (b) to give the corresponding hydroxy substituted derivatives of formula IV.

In the preferred embodiment, the treating in step (c) comprises contacting the compound formed in step (b) with a reducing agent such as $LiAlH_4$, $NaBH_4$—LiCl, $NaBH_4$—$BF_3$, $AlH_3$ and catalytic hydrogenation (10% Pd/C, $H_2$), and the like, in an ether such as ethyl ether, tetrahydrofuran, dioxane, diglyme and the like at a temperature range of —20° C. to 60° C. for a period of 0.5 hour to 1 day.

The O-alkylated compounds of formula III, wherein $R^1$ is an alkoxycarbonylalkyl group having the formula —$(CH_2)_nCOOR$, wherein n=1–4 and R is a methyl or ethyl group and $R^2$ is hydrogen, are prepared from the N-protected 3-(9-acridinylamino)-5-hydroxyaniline derivatives by following the same procedure for the N,O-alkylation of compound formed in step (a) as described above. The amino function of 3-(9-acridinylamino)-5-hydroxyaniline is more reactive than the hydroxy function and can be selectively protected. For example, treatment of 3-(9-acridinylamino)-5-hydroxyaniline (formula II) with acetic anhydride in the presence of base such as sodium methoxide, sodium ethoxide, potassium carbonate and the like in alcohol such as methanol, ethanol, and N,N-dimethylformamide and the like at room temperature gives N-acetyl-3-(9-acridinylamino)-5-hydroxyaniline. The N-acetylated compound is then reacted with an ω-haloalkyl carboxylic acid ester by following the same procedure as described above to give the O-alkylated N-acetyl compound. Removal of N-protecting group will give the O-alkylated 3-(9-acridinylamino)-5-hydroxyaniline derivatives.

The treating in step (d) comprises the halogenation of the compounds of formula IV to give the haloalkyl substituted compounds of formula V.

In the preferred embodiment, the treating in step (d) comprises contacting the compound formed in step (c) with halogenating agents such as benzyltriphenoxyphosphonium chloride [$PH_2P^+(PhO)_3Cl^-$], triphenylphosphonium/$CCl_4$, dichlorophenylphosphorane ($Ph_3PCl_2$), dibromophenylphosphorane ($Ph_3Br_2$), N-bromosuccinimide/$Ph_3P$, methyltriphenoxyphosphonium iodide [$(PhO)_3P.MeI$] and the like in a solvent at a temperature range of 0° C. to 100° C. for a period of 30 minutes to 1 day. The solvent is chloroform, dichloromethane, dichloroethane, ethyl ether, dioxane, diglyme, tetrahydrofuran, N,N-dimethylformamide and the like.

The treating in step (e) comprises the N- and/or O-acylation of the compounds of formula I to give the N- and/or O-acylated compounds of formula I, wherein $R^1$ and $R^2$ are the same or different and are hydrogen, an acetyl group, an ω-acetoalkylcarbonyl group having the formula —$CO(CH_2)_nCOCH_3$, wherein n=1–3, or an ω-acetoalkylcarbonyl group having the formula —$CO(CH_2)_2COOR$, wherein R is hydrogen, an alkali metal such as Na, K, or ammonium group.

In the preferred embodiment, the N,O-diacylated compound of formula I is synthesized by treatment of 3-(9-acridinylamino)-5-hydroxymethylaniline with an acid anhydride such as acetic anhydride, acetoacetic anhydride, levulinic anhydride, succinic anhydride, glutaric anhydride, and the like, in the presence of metal alkoxide such as sodium methoxide, sodium ethoxide, potassium tert-butoxide and the like, and an organic base such as triethylamine, N,N-diethylaniline, 4-dimethylaminopyridine, and the like in a solvent at a temperature range of 0° C. to 100° C. for a period of one hour to 4 days. The solvent is an alcohol such as methanol, ethanol, n-propanol, tert-butanol, and the like, or an ether such as tetrahydrofuran, dioxane, diglyme and the like or pyridine. Preferably, the reaction is preformed by treatment with 4-dimethylaminopyridine in the presence of DDC in pyridine at room temperature for 2 days.

In another preferred embodiment, the N-acylated compound of formula I is prepared by alkaline hydrolysis of the N,O-diacylated compound of formula I to give the corresponding N-acylated derivative by treatment with a metal hydroxide such as sodium hydroxide, potassium hydroxide and the like, or a metal alkoxide such as sodium methoxide, sodium ethoxide and the like in a solvent at a temperature range of 0° C. to 100° C. for a period of 30 minutes to 4 days. Preferably, the hydrolysis is performed in methanolic sodium methoxide at room temperature for 2 days.

In the preferred embodiment, the O-acylated compound is synthesized by treatment of 3-(9-acridinylamino)-5-hydroxymethylaniline (formula II) with acyl chloride such as acetyl chloride, acetoacetyl chloride, levulinyl chloride, acetylbutyryl chloride, succinyl chloride and the like, in the presence of an acid at a temperature range of 50° C. to 150° C. for a period of 20 minutes to 1 day. The acid is hydrogen chloride, hydrogen bromide, p-toluenesulfonic acid and the like.

In another preferred embodiment, the N-acylated compounds are prepared by reaction of 3-(9-acridinylamino)-5-hydroxyaniline with acyl chloride in concentrated aqueous ammonia at a temperature range of −10° C. to 30° C. Alternatively, the N-acylated compounds are also synthesized by treatment with an acid anydride such as acetic anhydride, acetoacetic anhydride, levulinoic anhydride, succinic anhydride, glutaric anhydride and the like, in the presence of a metal alkoxide such as sodium methoxide, sodium ethoxide, potassium tert-butoxide and the like, in a solvent at a temperature range of 0° C. to 100° C. for a period of one hour to 4 days. The solvent is an alcohol such as methanol, ethanol, n-propanol, tert-butanol and the like, or an ether such as tetrahydrofuran, dioxane, diglyme and the like.

In another preferred embodiment, the N,O-diacylated compound is prepared by treatment of the same starting material with an acid anhydride such as acetic anydride, acetoacetic anhydride, levulinoic anhydride, succinic anhydride, glutaric anhydride and the like, in pyridine, triethylamine, N,N-diethylaniline, 4-(N,N-dimethylamino)pyridine and the like at a temperature of 0° C. to 40° C. for a period of 1 hour to 3 days.

Upon completion of the reaction, the mixture is poured into water, neutralized with diluted acid such as hydrochloric acid, sulfuric acid, or acetic acid and the like. The precipitated product is collected by filtration, followed by purification by either recrystallization or chromatography. If no precipitated product appears after neutralization, the mixture is extracted with an organic solvent such as chloroform, dichloromethane, ethyl acetate, or ether. The product is obtained by crystallization or chromatography.

The treating in step (e) also comprises the saponification of the compounds formed in step (b) (formula III) to give the corresponding free carboxylic acids and their metal salts of formula I, wherein $R^1$ and $R^2$ are the same or different and are an alkyl group having the formula —$(CH_2)_n$COOR, wherein $n=1-4$ and R is hydrogen, Na, K, or ammonium.

In the preferred embodiment, the saponification of the compound formed in step (b) is performed in the following way. For example, the free acid is obtained upon treatment of the compound of the formula III with sodium hydroxide in a mixture of alcohol and water, or with iodotrimethylsilane in chloroform and the like. Treatment of the free carboxylic acid derivatives with one equivalent of base such as sodium hydroxide, potassium hydroxide or ammonium hydroxide gives the corresponding salts.

The treating in step (e) also comprises the N-sulfonylation of the compound of formula II by treatment with alkylsulfonyl chloride to form the corresponding N-alkylsulfone derivatives of formula I, wherein $R^1$ is hydrogen and $R^2$ is an alkylsulfonyl group (—$SO_2R$), wherein R is an alkyl group having 1 to 5 carbon atoms.

In the preferred embodiment, the treating comprises contacting the compound of formula II with an alkylsulfonyl chloride such as methanesulfonyl chloride, ethanesulfonyl chloride and the like in the presence of base such as sodium carbonate, potassium carbonate, sodium bicarbonate, potassium bicarbonate, metal alkoxide such as sodium methoxide, sodium ethoxide, potassium t-butoxide and the like, in a solvent at a temperature range of 30° C. to 120° C. for a period of 30 minutes to 1 day. The solvent is water, alcohol such as methanol, ethanol, n-propanol and the like.

The treating in step (e) comprises the conversion of the compound of formula V into the N- and/or O-alkylsulfonylalkyl compounds of formula I, wherein $R^1$ and/or $R^2$ are —$(CH_2)_nSO_2R$, wherein $n=1-4$ and R is an alkyl group having 1 to 5 carbon atoms.

In one embodiment, the treating in step (e) comprises contacting the compound formed in step (d) with sodium hydrosulfide or thiourea to give the corresponding thiol compounds of formula I, wherein $R^1$ and/or $R^2$ are —$(CH_2)_n$SH and $n=1-4$, which are then treated with alkyl halide such as methyl iodide, ethyl iodide, propyl iodide and the like, or with dialkylsulfate such as dimethylsulfate, diethylsulfate and the like in the presence of base such as sodium hydride, sodium hydroxide, potassium hydroxide, or a metal alkoxide such as sodium methoxide, sodium ethoxide and the like, to form dialkyl sulfides of formula I, wherein $R^1$ and/or $R^2$ are —$(CH_2)_n$SR, wherein $n=1-4$ and R is an alkyl group having 1 to 5 carbon atoms. Alternatively, the dialkyl sulfide derivatives are sythesized by treatment of the compound of formula II with allyl chloride to give the compounds of formula I, wherein $R^1$ and/or $R^2$ are —$CH_2CH=CH_2$, which are then allowed to react with an alkyl thiol such as methylthiol, ethylthiol, propylthiol and the like in the presence of hydrogen peroxide to form dialkyl sulfides. The dialkyl sulfides are then oxidized to give sulfonyl compounds of formula I by treatment with an oxidizing agent such as hydrogen peroxide, peracids, oxygen, ozone, organic peroxide, potassium permanganate, potassium persulfate, sodium hypochlorite and the like.

The treating in step (e) also comprises the conversion of the halogen derivatives formed in step (d) with formula V into their corresponding sulfonic acid or sulfonic acid salts of formula I, wherein $R^1$ and/or $R^2$ are —$(CH_2)_nSO_3M$ wherein M is hydrogen, sodium, potassium, or ammonium.

In one embodiment, the treating in step (e) comprises contacting the compound formed in step (d) with sodium bisulfide or potassium bisulfide in water at a temperature range of 40° C. to 100° C. for a period of 2 hours to 3 days. Upon cooling, a precipitate of the metal sulfonic acid salt appears. The product is collected by filtration and washed with ether and dried. If the product does not precipitate, the reaction mixture is evaporated in vacuo to dryness and the product is purified by repeated fractional crystallization from a 75% aqueous solution of the sulfonic acid salt by treatment with diluted acid or with a suitable cation exchange resin (in hydrogen form), until the free sulfonic acid is obtained.

In a similar manner, the sulfonic acid compound of formula I, wherein $R^1$ is $SO_2H$, $SO_2K$ or $SO_2NH_4$ and $R^2$ is hydrogen, is prepared from the compound of formula II via halogenation and sulfonation.

The alternative methods for the preparation of the sulfonic acid compound of formula I are: 1) oxidation of the alkyl thiols (see above) by treatment with potassium permanganate, chromic acid, nitric acid, bromine-$H_2O$, and hydrogen peroxide, and 2) reaction of the allyl substituted compound of formula I, wherein $R^1$ and/or $R^2$ are $-CH_2-CH=CH_2$ (see above) with sodium bisulfite by free radical process, or with thiolacetates followed by hydrogen peroxide-acetic acid oxidation.

The present invention also provides a pharmaceutical composition which comprises an amount of a compound of any of formulas I, II, III, IV, or V and a pharmaceutically acceptable carrier. In the preferred embodiment, the amount is enough compound to effectively inhibit growth of tumor cells. Preferably, the dose ranges from 1 to 500 mg/kg. Preferably, the compound has the structure of formula I wherein $R^1$ is H and $R^2$ is H; $R^1$ is $CO(CH_2)_2COMe$ and $R^2$ is $CO(CH_2)_2COMe$; $R^1$ is H and $R^2$ is $CO(CH_2)_2COMe$; $R^1$ is $CO(CH_2)_2COOH$ and $R^2$ is $CO(CH_2)_2COOH$; or $R^1$ is H and $R^2$ is $CO(CH_2)_2COOH$.

The term "pharmaceutically acceptable carrier" encompasses any of the standard pharmaceutical carriers such as sterile solutions, tablets, coated tablets, and capsules. Typically, such carriers contain excipients such as starch, milk, sugar, certain types of clay, gelatin, stearic acid, talc, vegetable fats or oils, gums, glycols, or other known excipients. Such carriers may also include flavor and color additives or other ingredients, such as compositions to increase solubility. Compositions which increase solubility include, but are not limited to, compounds which react with the hydrophobic regions of the subject compounds. Specifically, some examples of suitable agents include Emulphor (a polyoxyethylated fatty acid which is water miscible and nontoxic when diluted 1:10 with either sterile water or sterile physiological saline solution) and polyvinylpyrrolidone. Compositions comprising such carriers are formulated by well known conventional methods.

The present invention also provides a method of inhibiting growth of tumor cells which comprises contacting the tumor cells with an effective amount of a compound of any of formulas I, II, III, IV, or V, effective to inhibit growth of tumor cells. The method may be performed both in vitro and in vivo. Preferably, the tumor cells are a leukemia, a Lewis lung carcinoma, a mammary adenocarcinoma, or a melanoma. Preferably, the compound used has the structure of formula I wherein $R^1$ is H and $R^2$ is H; $R^1$ is $CO(CH_2)_2COMe$ and $R^2$ is $CO(CH_2)_2COMe$; $R^1$ is H and $R^2$ is $CO(CH_2)_2COMe$; $R^1$ is $CO(CH_2)_2COOH$ and $R^2$ is $CO(CH_2)_2COOH$; or $R^1$ is H and $R^2$ is $CO(CH_2)_2COOH$.

When performed in vivo, the administration of the compound may be effected by any of the well known methods, including but not limited to oral, intravenous, intramuscular, and subcutaneous. The method, amount and frequency of delivery are expected to vary according to the situation, and will depend on which carrier is used, and what result is desired. However, those variables are readily determinable by one skilled in the art.

The following Experimental Details section and Examples are set forth to aid in an understanding of the invention. These examples are not intended to, and should not be construed to, limit in any way the invention set forth in the claims which follow thereafter.

EXPERIMENTAL DETAILS

Example 1

To a suspension of sodium hydride (1.713 g, 71.4 mmol) in dry N,N-dimethylformamide (DMF) (60 mL) is added portionwise 3,5-diaminobenzyl-alcohol dichloride (6.10 g, 28.6 mmol) and stirred at room temperature for 15 minutes. A solution of 9-chloroacridine (5.02 g, 23.5 mmol) in dry DHF (50 mL) is then added dropwise into the mixture. The reaction mixture is stirred at room temperature for 4 hours and then poured into ice-water (600 mL) and acidified with acetic acid to pH 4.0. The precipitated product is collected by filtration, washed well with water and dried. The solid was treated with a boiling mixture of chloroform-methanol (10:1, 200 mL×4) and recrystallized from MeOH-DMF to 3-(9-acridinylamino)-5-hydroxymethylaniline, 5.56 g (75%), mp 282°–284° C. $^1$H-NMR (DMSO-$d_6$): δ 4.37 (2H, broad singlet, $\underline{CH_2}$—OH), 5.17 (1H, br, OH), 6.43–6.48 (2H, m, H-2 and H-4), 6.61 (1H, d, J=1.98 Hz, H-6), 7.23–7.51 (2H, m, ArH), 7.86–8.11 (4H, m, ArH), 8.31 (2H, d, J=8.78 Hz, ArH). Analyses: Calculated for $C_{20}H_{17}N_3O.\frac{1}{2}H_2O$: C, 74.05; H, 5.60; N, 12.95. Found: C, 73.87; H, 5.62; N, 12.67.

Example 2

A mixture of 3-(9-acridinylamino)-5-hydroxymethylaniline (250 mg, 0.79 mmol), levulinic acid anhydride (290 mg, 2.5 mmol), 4-dimethylaminopyridine (150 mg, 1.19 mmol) and 1,3-dicyclohexyl-carbodiimide (259 mg, 1.25mmol) in pyridine (2 mL) is stirred at room temperature for 2 days. The mixture is evaporated in vacuo, and the residue is coevaporated with ethanol (10 mL×3) to dryness. The residue is triturated with water (25 mL) and extracted with chloroform (25 mL×4). The chloroform extracts are combined, washed with water, dried ($Na_2SO_4$) and evaporated in vacuo to dryness.

The residue is chromatographed over a silica gel column (2×20 cm) using $CH_2Cl_2$/MeOH (v/v 98:2) as the eluent. The main product is collected to give N,O-bis (acetonylacetyl)-3-(9-acridinylamino)-5-hydroxymethylaniline as a foam, 181 mg (45%). $^1$H-NMR (DMSO-$d_6$): δ 2.07, 2.10 (each 3H, m, 2×$COCH_3$), 2.51, 2.66 (each 4H, m, 2×$COCH_2CH_2CO$), 4.96 (2H, s, Ph—$CH_2$—O), 6.43 (1H, broad singlet, ArH), 6.90–7.04 (2H, m, ArH), 6.95 (1H, broad singlet, ArH), 7.20 (1H, broad singlet, ArH), 7.51–7.86 (4H, m, ArH), 8.29–8.50 (2H, m, ArH), 9.86 (1H, s, NH). Analyses: Calculated for $C_{30}H_{27}N_3O_5$: C, 70.71; H, 5.34; N, 8.25. Found: C, 70.85; H, 5.41, N, 8.11.

By following the same procedure, the following N,O-acylated compounds of formula I are synthesized:

3-(9-acridinylamino)-N,O-bis(acetyl)-5-hydroxymethylaniline, 3-(9-acridinylamino)-N,O-bis(acetoacetyl)-5-hydroxymethylaniline, 3-(9-acridinylamino)-N,O-bis(acetonylethylcarbonyl)-5-hydroxymethylaniline, 3-(9-acridinylamino)-N,O-bis(acetonylpropionyl)-5-hydroxymethylaniline, 3-(9-acridinylamino)-N,O-bis(acetonylbutanoyl)-5-hydroxymethylaniline, 3-(9-acridinylamino)-N,O-bis(malonyl)-5-hydroxymethylaniline, 3-(9-acridinylamino)-N,O-bis(succinyl)-5-hydroxymethylaniline, and 3-(9-acridinylamino)-N,O-bis(glutaryl)-5-hydroxymethylaniline.

Example 3

A mixture of N,O-bis(acetonylacetyl)-3-(9-acridinylamino)-5-hydroxymethylaniline (423 mg, 0.83 mmol) in methanolic sodium methoxide [prepared from sodium (15 mg, 0.65mmol) in MeOH (15 mL)] is stirred at room temperature for 2 days. The mixture is passed through an ion-exchange resin (Dowex 50 in pyridine form). The product is eluted with a mixture of pyridine/H$_2$O (v/v 1:1). The combined eluate is evaporated in vacuo to dryness. The product is purified by chromatography (SiO$_2$, CHCl$_3$/MeOH, v/v 15:1) to give N-acetonylacety-3-(9-acridinylamino)-5-hydroxymethylaniline, 217 mg (64.0%), mp 197°-199° C. $^1$H-NMR (DMSO-d$_6$): δ 2.10 (3H, s, COCH$_3$), 4.35 (2H, broad singlet, CH$_2$—OH), 6.42 (1H, broad singlet, ArH), 6.90 (1H, broad singlet, ArH), 6.89-7.18 (2H, m, ArH), 7.19 (1H, broad singlet, ArH), 7.50-7.76 (4H, m, ArH), 8.30-8.48 (2H, m, ArH, 9.76 (1H, s, NH). Analyses: Calculated for C$_{25}$H$_{23}$N$_3$O$_3$: C, 72.62; H, 5.61; N, 10.16. Found: C, 72.53; H, 5.46; N, 9.99.

By following the same procedure, the following N-acylated compounds of formula I were synthesized:
3-(9-acridinylamino)-5-hydroxymethyl-N-acetylaniline,
3-(9-acridinylamino)-5-hydroxymethyl-N-acetoacetylaniline,
3-(9-acridinylamino)-5-hydroxymethyl-N-acetonylethylcarbonylaniline,
3-(9-acridinylamino)-5-hydroxymethyl-N-acetonylpropionylaniline,
3-(9-acridinylamino)-5-hydroxymethyl-N-acetonylbutanoylaniline,
3-(9-acridinylamino)-5-hydroxymethyl-N-malonylaniline,
3-(9-acridinylamino)-5-hydroxymethyl-N-succinylaniline, and
3-(9-acridinylamino)-5-hydroxymethyl-N-glutarylaniline.

Discussion

9-Anilinoacridines generally undergo nucleophilic attack by thiols forming inactive protein adducts linked by a thiol group to the C-9 position of the acridine or to the C-5' position of the aniline. The compounds of this invention are designed to withstand rapid degradation of the 9-anilinoacridines under biological conditions.

Table 1 lists typical results of in vitro studies on 3-(9-acridinylamino)-5-hydroxymethylaniline derivatives of formula I against growth of mouse leukemia L1210 and human leukemia HL-60 cells. The inhibitory activity of these compounds of formula I against topoisomerase II are also studied.

Table 2 lists typical examples of chemotherapeutic effects of 3-(9-acridinylamino)-5-hydroxymethylaniline derivatives of formula I on L1210 tumor bearing BDF$^1$ mice in vivo.

TABLE 1

The in vitro cytotoxicity of 3-(9-acridinylamino)-5-hydroxymethylaniline derivatives of formula I against growth of mouse leukemia L1210 and human leukemia HL-60 cells.

| Compound | R$^1$ | R$^2$ | IC$_{50}$ for Cell growth Inhibition L1210 (μM) | HL60 (μM) | Inhibition of Topo II with k-DNA decatenation assay |
|---|---|---|---|---|---|
| Ia | H | H | 0.026 | 0.097 | +++ |
| Ib | CO(CH$_2$)$_2$COMe | CO(CH$_2$)$_2$COMe | 0.098 | 0.003 | ++++ |
| Ic | H | CO(CH$_2$)$_2$COMe | 0.073 | 0.005 | +++ |
| Id | CO(CH$_2$)$_2$COOH | CO(CH$_2$)$_2$COOH | 2.0 | 0.859 | — |
| Ie | H | CO(CH$_2$)$_2$COOH | 1.07 | 0.999 | + |
| m-AMSA | | | 0.004 | 0.08 | +++ |

TABLE 2

Typical examples of chemotherapeutic effects of 3-(acridinylamino)-5-hydroxymethylaniline derivatives of formula I on L1210 tumor bearing BDF$^1$ mice.$^a$

| Compound | Dose$^b$ (mg/kg) | Average weight change (grams) Day 7 | Day 11 | Average survival time (days) | % Increase in lifespan$^c$ |
|---|---|---|---|---|---|
| control (Vehicle treated) | — | +2.0 | / | 7.2 | 0 |
| Ia | 5 | +1.0 | +2.0 | 14.0 | 94 |
|  | 10 | −0.5 | +0.0 | 15.0 | 108 |
| Ib | 5 | +2.0 | / | 9.0 | 25 |
|  | 10 | +2.0 | / | 11.0 | 53 |
|  | 20 | −3.0 | −4.0 | 14.0 | 94 |
| Ic | 5 | +2.0 | / | 11.0 | 53 |
|  | 10 | +1.5 | / | 9.0 | 25 |
|  | 20 | −1.5 | −2.0 | 21.0 | 192 |

$^a$Female mice, 19–21 grams, inoculated with 10$^6$ L1210 cells i.p. treatment schedule was day 1, QD × 4 + Day 7, QD × 2, i.p. (total 6 doses).
$^b$Lethal Doses of these compounds to BDF$^1$ mice have been determined:
Ia: 20 mg/kg, i.p., QD Day 1-Day 4 + Day 7;
Ib: 50 mg/kg, i.p., QD Day 1-Day 4, Day 7-Day 8;
Ic: 50 mg/kg i.p., QD Day 1-Day 4, Day 7-Day 8.
$^c$Increase in life span of 25% or greater indicates therapeutic activity.

The process of treating tumors according to this invention comprises administering to a warm blooded animal having an abnormal proportion of leukocytes or other evidences of malignancy, a therapeutic nontoxic amount of a compound of the invention such as 3-(9-acridinylamino)-5-hydroxymethylaniline, as such or in a form of a pharmaceutically acceptable salt thereof. The invention also provides a pharmaceutical composition in dosage unit form comprising from 1 to 500 mg/kg of a compound of the invention, per dosage unit, together with pharmaceutically acceptable nontoxic inert carrier of diluent thereof as described above.

What is claimed is:

1. A compound selected from the group consisting of:
3-(9-acridinylamino)-5-hydroxymethylaniline,
3-(9-acridinylamino)-5-hydroxymethyl-N-acetylaniline,
3-(9-acridinylamino)-N,O-bis(acetyl)-5-hydroxymethylaniline,
3-(9-acridinylamino)-5-acetoacetoxymethyl-N-acetylaniline,
3-(9-acridinylamino)-5-hydroxymethyl-N-acetoacetylaniline, 3-(9-acridinylamino)-N,O-bis(acetoacetyl)-5-hydroxymethylaniline,
3-(9-acridinylamino)-5-acetonylacetyloxymethylaniline,
3-(9-acridinylamino)-5-hydroxymethyl-N-acetonylacetylaniline
3-(9-acridinylamino)-N,O-bis(acetonylacetyl)-5-hydroxymethylaniline,
3-(9-acridinylamino)-5-acetonylpropionyloxymethylaniline,
3-(9-acridinylamino)-5-hydroxymethyl-N-acetonylpropionylaniline,
3-(9-acridinylamino)-N,O-bis(acetonylpropionyl)-5-hydroxymethylaniline,
3-(9-acridinylamino)-5-acetonylbutanoyloxymethylaniline,
3-(9-acridinylamino)-5-hydroxymethyl-N-acetonylbutanoylaniline,
3-(9-acridinylamino)-5-acetonylbutanoyloxymethyl-N-acetonylbutanoylaniline,
3-(9-acridinylamino)-5-malonyloxymethylaniline,
3-(9-acridinylamino)-5-hydroxymethyl-N-malonylaniline,
3-(9-acridinylamino)-5-malonyloxymethyl-N-malonylaniline,
3-(9-acridinylamino)-5-succinyloxymethylaniline,
3-(9-acridinylamino)-5-hydroxymethyl-N-succinylaniline,
3-(9-acridinylamino)-5-succinyloxymethyl-N-succinylaniline,
3-(9-acridinylamino)-5-glutaryloxymethylaniline,
3-(9-acridinylamino)-5-hydroxymethyl-N-glutarylaniline,
3-(9-acridinylamino)-5-glutaryloxymethyl-N-glutarylaniline,
3-(9-acridinylamino)-5-aminobenzyloxyacetic acid,
3-(9-acridinylamino)-5-hydroxymethylanilinoacetic acid,
sodium 3-(9-acridinylamino)-5-hydroxymethylanilinoacetate,
3-(9-acridinylamino)-N,O-bis(hydroxycarbonylmethyl)-5-hydroxymethylaniline,
3-[3-(9-acridinylamino)-5-aminobenzyloxy]propionic acid,
sodium 2-[3-(9-acridinylamino)-5-acetamidobenzyloxy]propionate,
3-[3-(9-acridinylamino)-5-hydroxymethylanilino]propionic acid,
sodium 2-[3-(9-acridinylamino)-5-hydroxymethylanilino]propionate
3-[3-(9-acridinylamino)-5-hydroxycarbonylethoxymethyl-anilino]propionic acid,
sodium 2-[3-(9-acridinylamino)-5-hydroxycarbonylethoxymethylanilino]propionate
4-[3-(9-acridinylamino)-5-acetamidobenzyloxy]butanoic acid,
sodium 3-(9-acridinylamino)-5-aminobenzyloxybutyrate,
4-[3-(9-acridinylamino)-5-hydroxymethylanilino]butanoic acid,
sodium 4-[3-(9-acridinylamino)-5-hydroxymethylanilino]butyrate,
4-[3-(9-acridinylamino)-5-hydroxycarbonylpropyloxymethylanilino]butanoic acid,
sodium 4-[3-(9-acridinylamino)-5-hydroxycarbonylpropyloxymethylanilino]butyrate,
4-[3-(9-acridinylamino)-5-hydroxycarbonylpropylmethylanilino]butanoic acid
sodium 4-[3-(9-acridinylamino)-5-hydroxycarbonylpropyloxymethylanilino]butyrate
N-[3-(9-acridinylamino)-5-hydroxymethylphenyl]-methanesulfonamide,
methyl 2-[3-(9-acridinylamino)-5-acetamidobenzyloxy]ethyl sulfone,
methyl 2-[3-(9-acridinylamino)-5-aminobenzyloxy]ethyl sulfone,
methyl 2-[3-(9-acridinylamino)-5-hydroxymethylanilino]ethyl sulfone,
3-(9-acridinylamino)-N,O-bis(methylsulfonylethyl)-5-hydroxymethylaniline,
methyl 3-[3-(9-acridinylamino)-5-aminobenzyloxy]propyl sulfone,
methyl 3-[3-(9-acridinylamino)-5-hydroxymethylanilino]propyl sulfone,
methyl 3-(9-acridinylamino)-N,O-bis(methylsulfonylpropyl)-5-hydroxymethylanaline,
3-[3-(9-acridinylamino)-5-aminobenzyloxy]propyl sulfonic acid,
3-[3-(9-acridinylamino)-5-hydroxymethylanilino]propyl sulfonic acid,
3-(9-acridinylamino)-N,O-bis(sulfonylpropyl)-5-hydroxymethylanaline,
sodium 3-[3-(9-acridinylamino)-5-aminobenzyloxy]propyl sulfinate,
sodium 3-[3-(9-acridinylamino)-5 -hydroxymethylanilino]propyl sulfinate,
3-(9-acridinylamino)-5-hydroxymethylaniline-N,O-bis(sodiumpropyl sulfinate),
methyl 2-[3-(9-acridinylamino)-5-aminobenzyloxy]ethyl sulfonate,
methyl 2-[3-(9-acridinylamino)-5-acetamidobenzyloxy]ethyl sulfonate,
methyl 2-[3-(9-acridinylamino)-5-hydroxymethylanilino]ethyl sulfonate,
methyl 3-(9-acridinylamino)-5-hydroxymethylaniline-N,O-bis-(ethyl sulfonate),
methyl 3-[3-(9-acridinylamino)-5-aminobenzyloxy]propyl sulfonate,
methyl 3-(9-acridinylamino)-5-acetamidobenzyloxy]propyl sulfonate,
methyl 3-[3-(9-acridinylamino)-5-hydroxymethylanilino]propyl sulfonate,
methyl 3-(9-acridinylamino)-5-hydroxymethylaniline-N,O-bis-(propyl sulfonate),
sodium 2-[3-(9-acridinylamino)-5-aminobenzyloxy]ethyl sulfonate,
sodium 2-[3-(9-acridinylamino)-5-acetamidobenzyloxy]ethyl sulfonate,
sodium 2-[3-(9-acridinylamino)-5-hydroxymethylaniline]ethyl sulfonate,
sodium 3-(9-acridinylamino)-5-hydroxymethylaniline-N,O-bis-(ethyl sulfonate),
sodium 3-[3-(9-acridinylamino)-5-aminobenzyloxy]propyl sulfonate,
sodium 3-[3-(9-acridinylamino)-5-acetamidobenzyloxy]propyl sulfonate,
sodium 3-[3-(9-acridinylamino)-5-hydroxymethylanilino]propyl sulfonate,
sodium 3-(9-acridinylamino)-5-hydroxymethylaniline-N,O-bis-(propyl sulfonate), or
3-(9-acridinylamino)-5-($\beta$-alanyloxyethoxymethyl)aniline.

2. A compound having the structure:

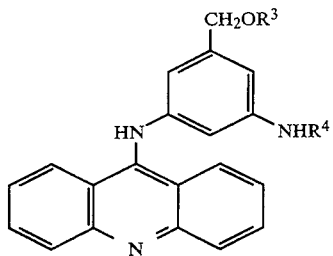

wherein $R^3$ and $R^4$ are independently the same or different and are hydrogen or an alkylester group having the formula —$(CH_2)_nCOOR$, wherein $n=1-4$ and R is an alkyl group having 1 to 4 carbon atoms.

3. A compound of claim 2 selected from the group consisting of:

3-(9-acridinylamino)-N-(ethoxycarbonylmethyl)-5-hydroxymethylaniline, 3-(9-acridinylamino)-N-acetyl-O-(ethoxycarbonylmethyl)-5-hydroxmethylaniline, 3-(9-acridinylamino)-O-(ethoxycarbonylmethyl)-5-hydroxymethylaniline, 3-(9-acridinylamino)-N,O-bis-(ethyoxycarbonylmethyl)-5-hydroxymethylaniline, 3-(9-acridinylamino)-N-(ethoxycarbonylethyl)-5-hydroxymethylaniline, 3-(9-acridinylamino)-N-acetyl-O-(ethoxycarbonylethyl)-5-hydroxymethylaniline, 3-(9-acridinylamino)-O-(ethoxycarbonylethyl)-5-hydroxymethylaniline, 3-(9-acridinylamino)-N,O-bis-(ethoxycarbonylethyl)-5-hydroxymethylaniline, 3-(9-acridinylamino)-N-(ethoxycarbonylpropyl)-5-hydroxymethylaniline, 3-(9-acridinylamino)-N-acetyl-O-(ethoxycarbonylpropyl)-5-hydroxymethylaniline, 3-(9-acridinylamino)-O-(ethoxycarbonylpropyl)-5-hydroxymethylaniline, 3-(9-acridinylamino)-N,O-bis-(ethoxycarbonylpropyl)-5-hydroxymethylaniline, 3-(9-acridinylamino)-N-(ethoxycarbonylbutyl)-5-hydroxymethylaniline, 3-(9-acridinylamino)-N-acetyl-O-(ethoxycarbonylbutyl)-5-hydroxymethylaniline, 3-(9-acridinylamino)-O-(ethoxycarbonylbutyl)-5-hydroxymethylaniline, or 3-(9-acridinylamino)-N,O-bis-(ethoxycarbonylbutyl)-5-hydroxymethylaniline.

* * * * *